United States Patent [19]

Markwalder et al.

[11] Patent Number: 5,260,325
[45] Date of Patent: Nov. 9, 1993

[54] ANGIOTENSIN II RECEPTOR BLOCKING TERTIARY AMIDES

[75] Inventors: Jay A. Markwalder; Richard S. Pottorf, both of Wilmington, Del.

[73] Assignee: E. I. Du Pont de Nemours and Company, Wilmington, Del.

[21] Appl. No.: 747,022

[22] Filed: Aug. 19, 1991

[51] Int. Cl.⁵ .................. C07D 257/04; A61K 31/41
[52] U.S. Cl. .................... 514/381; 548/253; 548/119
[58] Field of Search .............. 548/253, 252, 119; 514/381

[56] References Cited

U.S. PATENT DOCUMENTS 4,898,949 2/1990 Wright et al. .................. 548/253

FOREIGN PATENT DOCUMENTS 0324377 8/1989 European Pat. Off. .
0443983 8/1991 European Pat. Off. .
047203 3/1972 Japan ......................... 548/254
0443983 8/1991 United Kingdom .

*Primary Examiner*—David B. Springer

[57] ABSTRACT

Novel substituted tertiary amides of formula (I), which are useful as angiotensin II antagonists, are disclosed:

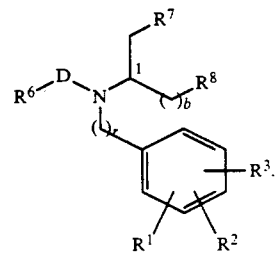

6 Claims, No Drawings

ANGIOTENSIN II RECEPTOR BLOCKING TERTIARY AMIDES

BACKGROUND OF THE INVENTION

Field of the Invention

This invention relates to novel substituted amides and processes for their preparation. These compounds inhibit the action of the hormone angiotensin II (AII) and are therefore useful in alleviating angiotensin induced hypertension. AII is the product of two enzymes, renin and angiotensin converting enzyme, acting on angiotensinogen and angiotensin I, respectively. This peptide hormone is a powerful vasopressor which has been implicated as a causative agent for producing high blood pressure in various mammalian species, such as the rat, dog, and man. The compounds of this invention block the action of AII at its receptors on target cells and thus prevent the increase in blood pressure produced by the hormone-receptor interaction. By administering a compound of this invention to a species of mammal with hypertension due to AII, the blood pressure is reduced.

Carini, et al. in EP 0 324 377 issued Aug. 29, 1989 discloses 1,2,4-trisubstituted imidazoles of the formula:

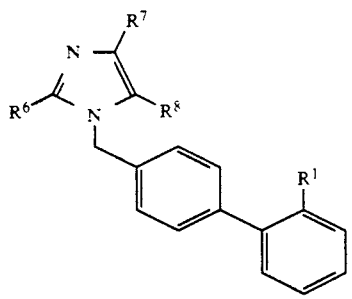

wherein $R^1$ is carboxylic acid or a suitable isostere; $R^6$ is lower alkyl, $R^7$ is alkyl; perfluoroalkyl, or aryl; and $R^8$ is hydroxymethyl, aldehyde, or carboxylic acid. These compounds block the action of AII on its receptor and do lower blood pressure.

Applicants have discovered that appropriately substituted amides are antagonists for the action of AII on its receptor similar to the imidazoles described in EP 0 324 377. Such compounds are not only interesting from a chemical viewpoint, but they also have pharmacological and medical utilities. Although many tertiary amides are known, these amides substituted as described below have not been disclosed previously.

SUMMARY OF THE INVENTION

Tertiary amides of the following formula (I) are antagonists of angiotensin II

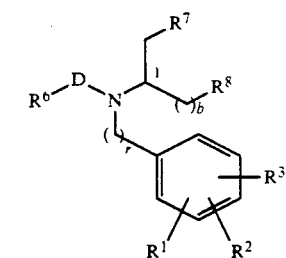

wherein:
$R^1$ is other than in the ortho position and is
(a) 4—$CO_2H$,
(b) —$CH_2CO_2H$,
(c) —$C(CF_3)_2OH$,
(d) —$CONHNHSO_2CH_3$,
(e) 4—$CONHCH(CO_2H)CH_2C_6H_5$ (L-isomer),
(f) 4—$CONHOR^{12}$,
(g) —$CONHSO_2R^{10}$,
(h) —$CONHSO_2NHR^9$,
(i) —$C(OH)R^9PO_3H_2$,
(j) —$NHCOCF_3$,
(k) —$NHCONHSO_2R^{10}$,
(l) —$NHPO_3H_2$,
(m) 4—$NHSO_2R^{10}$,
(n) —$NHSO_2NHCOR^{10}$,
(o) —$OPO_3H_2$,
(p) —$OSO_3H$,
(q) —$PO_3H_2$,
(r) —$PO(OH)R^9$,
(s) —$SO_3H$,
(t) —$SO_2NHR^9$,
(u) —$SO_2NHCOR^{10}$,
(v) —$SO_2NHCONHR^9$,

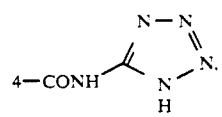 (w)

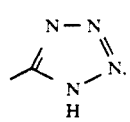 (x)

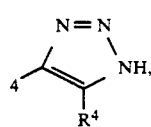 (y)

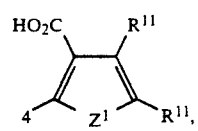 (z)

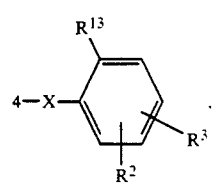 (aa)

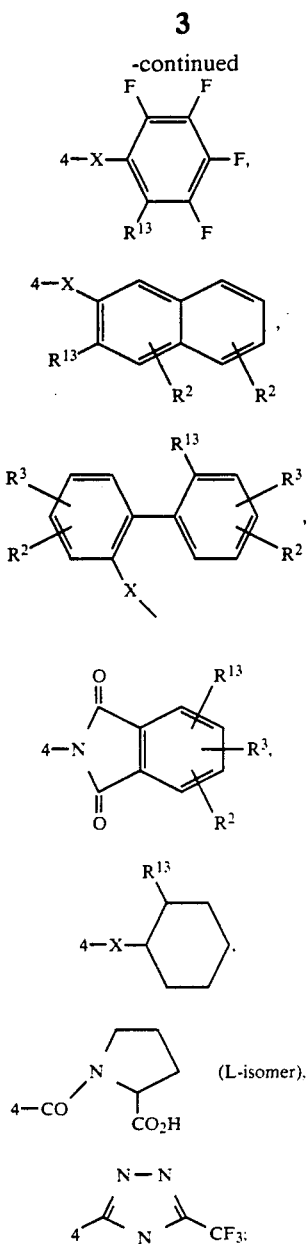

-continued

R² is
(a) H,
(b) halo (F, Cl, Br, I),
(c) C₁-C₄ alkyl,
(d) C₁-C₄ alkoxy,
(e) C₁-C₄ acyloxy,
(f) C₁-C₄ alkylthio,
(g) C₁-C₄ alkylsulfinyl,
(h) C₁-C₄ alkylsulfonyl,
(i) hydroxy (C₁-C₄) alkyl,
(j) aryl (C₁-C₄) alkyl,
(k) —CO₂H,
(l) —CN,
(m) tetrazol-5-yl,
(n) 'CONHOR¹²,
(o) —SO₂NHR⁹,
(p) —NH²,
(q) C₁-C₄ alkylamino,
(r) C₁-C₄ dialkylamino,
(s) —NHSO₂R¹⁰,
(t) —NO₂,
(u) furyl,
(v) aryl;
wherein aryl is phenyl optionally substituted with one or two substituents selected from the group consisting of halo, C₁-C₄ alkyl, C₁-C₄ alkoxy, -NO₂, —CN, —CF₃, C₁-C₄ alkylthio, —OH, —NH², C₁-C₄ alkylamino, C₁-C₄ dialkylamino, —CO₂H, —CO₂CH₃, —CO₂CH₂CH₃, —CO₂CH₂phenyl;

R³ is
(a) H,
(b) halo,
(c) C₁-C₄ alkyl,
(d) C₁-C₄ alkoxy,
(e) C₁-C₄ alkoxyalkyl;

R⁴ is
(a) —CN,
(b) —NO₂,
(c) —CO₂R¹¹;

R⁵ is
(a) H,
(b) C₁-C₆ alkyl,
(c) C₃-C₆ cycloalkyl,
(d) C₂-C₄ alkenyl,
(e) C₂-C₄ alkynyl;

R⁶ is
(a) C₁-C₁₀ alkyl,
(b) C₃-C₁₀ alkenyl,
(c) C₃-C₁₀ alkynyl,
(d) C₃-C₈ cycloalkyl,
(e) C₄-C₈ cycloalkenyl,
(f) C₄-C₁₀ cycloalkylalkyl,
(g) C₅-C₁₀ cycloalkylalkenyl,
(h) C₅-C₁₀ cycloalkylalkynyl,
(i) —(CH₂)ₛZ²(CH₂)ₘR⁵,
(j) benzyl, optionally substituted on the phenyl ring with 1-2 substituents selected from the group of halo, C₁-C₄ alkyl, C₁-C₄ alkoxy, —OH or —NO₂,
(k) CH₂-heterocyclic,
wherein heterocyclic is a 5-membered ring containing N or S and optionally substituted with one or two substituents selected from the group consisting of halo, C₁-C₄ alkyl and C₁-C₄ alkoxy;

R⁷ is
(a) C₁-C₆ alkyl,
(b) C₃-C₆ cycloalkyl,
(c) C₂-C₁₀ perfluoroalkyl,
(d) COR³⁰,
(e) aryl,
(f) C₁-C₃ alkylaryl,
(g) —(CH₂)ₙS(O)ₘCH₂phenyl, where phenyl is optionally substituted with 1-2 substituents selected from the group of halo, —OH, C₁-C₃ alkoxy, or C₁-C₃ alkyl,
(h) —CH₂S(O)ₘCH₃,
(i) 1-, 2-, or 3-indolyl,
(j) 2-, 3-, or 4-quinolinyl or isoquinolinyl,
wherein aryl is as defined above and 1- or 2-naphthyl;

R⁸ is
(a) —CO₂H,
(b) —CO₂R⁴⁰,
(c) —CHO,
(d) —CH₂OH,
(e) —CH₂OC(O)(CH₂)ₙCO₂H,
(f) —CN,
(g) —SO₃H, (h) —SO$_2$OR$^{40}$,
(i) -tetrazol-5-yl,
(j) —PO$_3$H$_2$,
(k) —P(O$_2$)OR$^{40}$;

R$^9$ is
(a) H,
(b) C$_1$-C$_5$ alkyl,
(c) aryl,
(d) —CH$_2$-aryl,
(e) heteroaryl, wherein aryl is as defined above, and heteroaryl is an unsubstituted, monosubstituted or disubstituted 5- or 6-membered aromatic ring which contains from 1 to 3 heteroatoms selected from the group consisting of O, N, and S and wherein the substituents are members selected from the group consisting of —OH, —SH, C$_1$-C$_4$ alkyl, C$_1$-C$_4$ alkoxy, —CF$_3$, halo, —NO$_2$, —CO$_2$H, —CO$_2$CH$_3$, —CO$_2$-benzyl, —NH$_2$, C$_1$-C$_4$ alkylamino, C$_1$-C$_4$ dialkylamino;

R$^{10}$ is
(a) aryl as defined above,
(b) C$_3$-C$_7$ cycloalkyl,
(c) C$_3$-C$_4$ perfluoroalkyl,
(d) C$_1$-C$_4$ alkyl optionally substituted with a substituent selected from the group consisting of aryl as defined above, heteroaryl as defined above, —OH, —SH, C$_1$-C$_4$alkyl, C$_1$-C$_4$ alkoxy, C$_1$-C$_4$ alkylthio, —CF$_3$, halo, —NO$_2$, —CO$_2$H, —CO$_2$CH$_3$, —CO$_2$-benzyl, —NH$^2$, C$_1$-C$_4$ alkylamino, C$_1$-C$_4$ dialkylamino, —PO$_3$H$_2$,
(e) heteroaryl as defined above;

R$^{11}$ is
(a) H,
(b) C$_1$-C$_6$ alkyl,
(c) C$_3$-C$_6$ cycloalkyl,
(d) phenyl,
(e) benzyl;

R$^{12}$ is
(a) H,
(b) CH$_3$,
(c) benzyl;

R$^3$ is
(a) —CO$_2$H,
(b) —CH$_2$CO$_2$H,
(c) —C(CH$_3$)$_2$OH,
(d) —CONHNHSO$_2$CF$_3$,
(e) —CONHOR$^{12}$,
(f) —CONHSO$_2$R$^{10}$,
(g) —CONHSO$_2$NHR$^9$,
(h) —C(OH)R$^9$PO$_3$H$_2$,
(i) —NHCOCF$_3$,
(j) —NHCONHSO$_2$R$^{10}$,
(k) —NHPO$_3$H$_2$,
(l) —NHSO$_2$R$^{10}$,
(m) —NHSO$_2$NHCOR$^{10}$,
(n) —OPO$_3$H$_2$,
(o) —OSO$_3$H,
(p) —PO(OH)R$^9$,
(q) —PO$_3$H$_2$,
(r) —SO$_3$H,
(s) —SO$_2$NHR$^9$,
(t) —SO$_2$NHCOR$^{10}$,
(u) —SO$_2$NHCONHR$^9$,

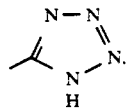 (v)

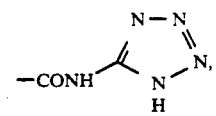 (w)

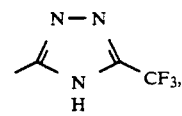 (x)

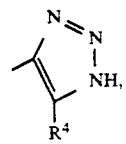 (y)

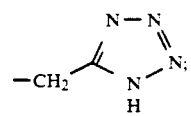 (z)

R$^{14}$ is
(a) H,
(b) C$_1$-C$_6$ alkyl,
(c) CH$_2$CH=CH$_2$,
(d) benzyl;

R$^{15}$ is
(a) H,
(b) C$_1$-C$_8$ alkyl,
(c) C$_1$-C$_8$ perfluoroalkyl,
(d) C$_3$-C$_6$ cycloalkyl,
(e) phenyl,
(f) benzyl;

R$^{16}$ is
(a) H,
(b) C$_1$-C$_6$ alkyl,
(c) benzyl;

R$^{17}$ is
(a) H,
(b) C$_1$-C$_6$ alkyl,
(c) C$_3$-C$_6$ cycloalkyl,
(d) phenyl,
(e) benzyl;

R$^{18}$ is
(a) —NR$^{19}$R$^{20}$—,
(b) —NHCONH$^2$,
(c) —NHCSNH$^2$,
(d) —NHSO$_2$-p-tolyl,
(e) —NHSO$_2$—C$_6$H$_5$;

R$^{19}$ and R$^{20}$ are independently
(a) H,
(b) C$_1$-C$_5$ alkyl,
(c) phenyl;

R$^{21}$ and R$^{22}$ are independently
(a) H,
(b) C$_1$-C$_4$ alkyl,
(c) or taken together are —(CH$_2$)$_q$—;

R$^{30}$ is
(a) H,
(b) C$_1$-C$_5$ alkyl,
(c) OR$^{12}$, (d) morpholino;

$R^{40}$
 (a) $C_1$-$C_6$ alkyl,
 (b) $C_1$-$C_6$ perfluoroalkyl,
 (c) 1-adamantyl,
 (d) 1-naphthyl,
 (e) benzyl;

D is (a) —CO—,
 (b) —CS—,
 (c) —SO$_2$—;

X is
 (a) a carbon-carbon single bond,
 (b) —CO—,
 (c) —C($R^{19}$)($R^{20}$)—,
 (d) ——,
 (e) —S—,
 (f) —SO—,
 (g) —SO$_2$—,
 (h) —NR$^{14}$—,
 (i) —CONR$^{16}$—,
 (j) —NR$^{16}$CO—,
 (k) OC($R^{19}$)($R^{20}$)—,
 (k) —OC($R^{19}$)($R^{20}$)O—,
 (l) —C($R^{19}$)($R^{20}$)O—,
 (m) —SC($R^{19}$)($R^{20}$)—,
 (n) —C($R^{19}$)($R^{20}$)S—,
 (o) —NHC($R^{19}$)($R^{20}$)—,
 (p) —C($R^{19}$)($R^{20}$)NH—,
 (q) —NR$^{16}$SO$_2$—,
 (r) —SO$_2$NR$^{16}$—,
 (s) —CH=CH—,
 (t) —CF=CF—,
 (u) —CF=CH—,
 (v) —CH=CF—,
 (w) —CH$_2$—CH$_2$—,
 (x) —CF$_2$CF$_2$—,
 (y) —CH(OR$^{15}$)—,
 (z) —CH(OCOR$^{17}$)—,
 (aa) —C(=NR$^{18}$)—,
 (bb) —C(OR$^{21}$)(OR$^{22}$)—,
 (cc) 1,2-cyclopropyl,
 (dd) 1,1-cyclopropyl;

$Z^1$ and $Z^2$ are independently
 (a) —O—,
 (b) —S—,
 (c) —NR$^{11}$—;

g is 0 to 2,
m is 1 to 5,
n is 0 to 1,
s is 0 to 5,
q is 2 to 3,
r is 1 to 2,
b is 0 to 2,
or a pharmaceutically acceptable salt thereof.

Preferred compounds of this invention, due to their activity as angiotensin II antagonists, are those of formula (I) wherein:

$R^1$ is in the para position and is:
 (a) —CO$_2$H,
 (b) —NHSO$_2$R$^{10}$,
 (c) —SO$_2$NHCOR$^{10}$,

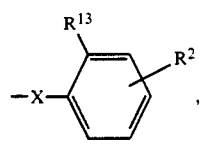
(d)

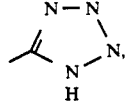
(e)

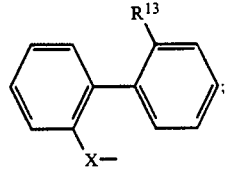
(f)

$R^3$ is H;
$R^6$ is
 (a) $C_1$-$C_{10}$ alkyl,
 (b) $C_3$-$C_{10}$ alkenyl,
 (c) $C_3$-$C_{10}$ alkynyl,
 (d) $C_3$-$C_8$ cycloalkyl,
 (e) CH$_2$-heterocyclic,
 (f) $C_2$-$C_7$ alkoxy,
wherein heterocyclic is a 5-membered ring containing N or S and optionally substituted with one or two substituents selected from the group consisting of halo, $C_1$-$C_4$ alkyl and $C_1$-$C_4$ alkoxy;

$R^7$ is
 (a) $C_2$-$C_3$ alkyl,
 (b) $C_2$-$C_3$ perfluoroalkyl,
 (c) phenyl optionally substituted with 1-2 substituents selected from the group consisting of —OH, —OCH$_3$, or $C_1$-$C_3$ alkyl, or halo,
 (d) —(CH$_2$)$_n$S(O)$_g$CH$_2$-phenyl optionally substituted with —CH3 or —OCH$_3$,
 (e) —CH$_2$S(O)$_g$CH$_3$;

$R_8$ is
 (a) CO$_2$H,
 (b) CO$_2$CH$_3$,
 (c) CO$_2$CH$_2$CH$_3$,
 (d) CO$_2$benzyl,
 (e) CHO,
 (f) CH$_2$OH;

$R^{13}$ is
 (a) —CO$_2$H,
 (b) —CONHSO$_2$R$^{10}$,
 (c) —NHCONHSO$_2$R$^{10}$,
 (d) —NHSO$_2$R$^{10}$,
 (e) —NHSO$_2$NHCOR$^{10}$,
 (f) —SO$_2$NHR$^9$,
 (g) —PO$_3$H$_2$,
 (h) —SO$_3$H,
 (i) —SO$_2$NHCOR$^{10}$,
 (j) —SO$_2$NHCONHR$^9$,

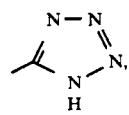
(k)

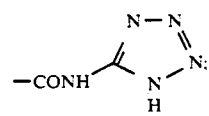
(l)

X is (a) a carbon-carbon single bond,
(b) —O—,
(c) —CO—,
(d) —S—,
(e) —CONR$^{16}$—,
(f) —NR$^{16}$CO—,
(g) -OCH$_2$—,
(h) —CH$_2$O—,
(i) —SCH$_2$—,
(j) —CH$_2$S—,
(k) —NHCH$_2$—,
(l) —CH$_2$NH—,
(m) —CH=CH—,
(n) —CH$_2$CH$_2$—;

r is 1;
or a pharmaceutically acceptable salt thereof.

Still more preferred are compounds of the above preferred scope wherein:

R$^2$ is
(a) H,
(b) halo
(c) C$_1$-C$_4$ alkyl,
(d) C$_1$-C$_4$ alkoxy;

R$^6$ is
(a) C$_2$-C$_7$ alkyl,
(b) C$_2$-C$_7$ alkoxy,
(c) CH$_2$-heterocyclic, wherein the heterocyclic ring is 5-membered N or S, and optionally substituted with one or more alkyl groups;

R$^8$ is
(a) —CO$_2$H,
(b) —CO$_2$CH$_3$,
(c) —CO$_2$CH$_2$CH$_3$,
(d) —CHO,
(e) —CH$_2$OH;

R$^{13}$ is
(a) —CO$_2$H,
(b) —CONHSO$_2$R$^{10}$,
(c) —NHCONHSO$_2$R$^{10}$,
(d) —NHSO$_2$R$^{10}$,
(e) —NHSO$_2$NHCOR$^{10}$,
(f) —SO$_2$NHR$^9$,
(g) —SO$_2$NHCOR$^{10}$,
(h) —SO$_2$NHCONHR$^9$,

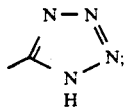

(i)

D is —CO—;
X is
(a) a carbon-carbon single bond,
(b) —O—,
(c) —CO—,
(d) —NHCO—,
(e) —OCH$_2$—;

b=0;
or a pharmaceutically acceptable salt thereof.

Most preferred due to their activity as angiotensin II antagonists are compounds of the more preferred scope above wherein
R$^1$ is

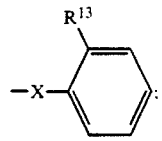

X is a carbon-carbon single bond; or a pharmaceutically acceptable salt thereof.

Illustrative of the most preferred compounds are the following:

(S)  N-valeryl-N-[(2'-(1H-tetrazol-5-yl)biphenyl-4-yl)methyl]-phenylalanine
(R)  N-butyryl-N-[(2'-(1H-tetrazol-5-yl)biphenyl-4-yl)methyl]-phenylalanine
(S)  N-butyryl-N-[(2'-(1H-tetrazol-5-yl)biphenyl-4-yl)methyl]-phenylalanine
(R)  N-isovaleryl-N-[(2'-(1H-tetrazol-5-yl)biphenyl-4-yl)methyl]-S-benzylcysteine
(R)  N-valeryl-N-[(2'-(1H-tetrazol-5-yl)biphenyl-4-yl)methyl]-S,S-dioxy-S-benzylcysteine
(R)  N-valeryl-N--[(2'-(1H-tetrazol-5-yl)biphenyl-4-yl)methyl]-norvaline.

Note that throughout the text when an alkyl substituent is mentioned, the normal alkyl structure is meant (e.g., butyl is n-butyl) unless otherwise specified. However, in the definition of radicals above (e.g., R$^6$), both branched and unbranched chains are included in the scope of alkyl, alkenyl and alkynyl. It is to be understood that the optical center 1 of formula (I) may be of the R or S configuration or a mixture of both.

Pharmaceutically acceptable salts include both the inorganic salts and organic salts; a list of which is given in Remington's Pharmaceutical Sciences, 17th Edition, page 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

DETAILED DESCRIPTION

Synthesis

The compounds of formula (I) may be prepared using the reactions and techniques described in this section. The reactions are performed in a solvent appropriate to the reagents and materials employed and suitable for the transformation being effected. It is understood by those skilled in the art of organic synthesis that the functionality present in the molecule must be consistent with the chemical transformations proposed. This will frequently necessitate judgement as to the order of synthetic steps, protecting groups required, and deprotection conditions. Throughout the following section, not all compounds of formula (I) falling into a given class may necessarily be prepared by all methods described for that class. Substituents on the starting materials may be incompatible with some of the reaction conditions required in some of the methods described. Such restrictions to the substituents which are compatible with the reactions will be readily apparent to one skilled in the art and alternative methods to those described must then be used.

Appendage of the various functionalites of formula (I) may require protecting groups; the choice, attachment, and removal of which is discussed in: Theodora W. Greene, "Protective Groups in Organic Synthesis" Wiley-Interscience.

The general synthesis of the compounds of formula (I) is outlined in Scheme 1. These compounds can be synthesized either by acylation of a secondary amine, 2, or a primary amine, 3, to give intermediates 4 and 5, respectively. The acylation can be accomplished by a number of methods including the reagents: sulfonyl chloride (when D=—$SO_2$—) or when D=—CO— the reagents can be acid chloride, acid anhydride, mixed carbonic acid anhydride, carbodiimides (dicyclohexylcarbodiimide, isopropylcarbodiimide or water-soluble carbodiimides), activated esters (nitrophenyl ester, pentafluorophenyl ester, N-hydroxysuccinic imido ester), Woodward reagent K, carbonyldiimidazole, or phosphorus coupling reagents such as BOP-Cl. The preferred acylation method is by the acid chloride or acid anhydride in dimethylformamide (DMF), THF, or $CH_2Cl_2$ with tertiary amine present. To prepare compounds of the invention where D=—CS—, compound 4 where D=—CO— may be treated with Lawesson's reagent, $P_2S_5$, or the like.

Alkylation of intermediate 5 will also give compounds of formula (I). This can be accomplished by treating 5 with a base such as NaH or the like followed by addition of the appropriately protected functionalized benzylic halides 6, mesylates, or tosylates. The preparation of these intermediates such as 6 is extensively described in EP 0 324 377 A2, EP 400 974, EP 401 030, U.S. Pat. No. 4,820,843, EP 400 835, and is incorporated herein by reference.

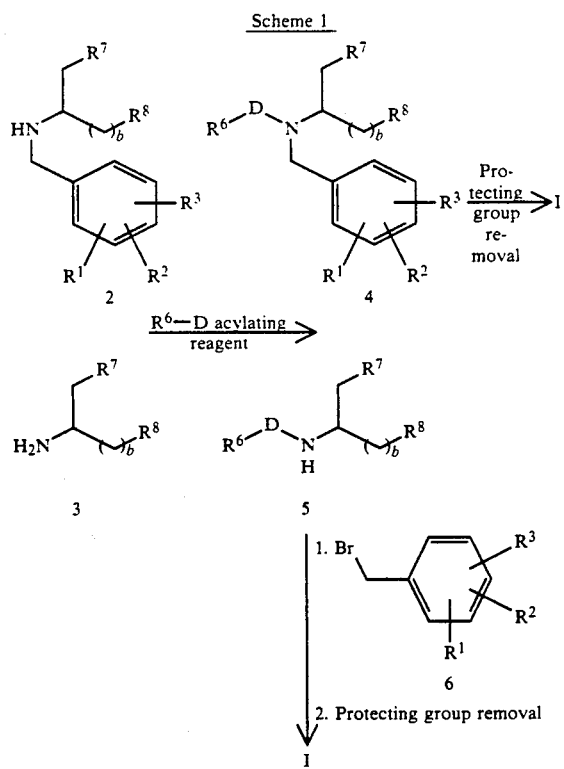

The preferred method is acylation of the secondary amine, 2, the synthesis of which is outlined in Scheme 2a. Alkylation of a primary amine of the general formula, 7, with 6 can be accomplished by prolonged stirring (1-5 days) in the presence of a base to give 2.

Alternatively, 2 can be obtained by reduction of the intermediate imine formed by treatment of 7 with the aldehyde, 8. These reductions can be accomplished by catalytic hydrogenation (See Rylander in "Catalytic Hydrogenation Over Platinum Metals," Academic Press, 1967, pp 291-303) or with the borohydride reducing agents (See Borch, et al., J. Am. Chem. Soc., 93, 2897 (1971); and Schellenberg, J. Org. Chem., 28, 3259 (1963)). Compounds such as 8 can be prepared from the corresponding halides, 6, by a number of procedures familiar to those skilled in the art. Preferably, the method described by Wilcox, et al., J. Org. Chem., 54, 2195 (1989) where the halide is oxidized by sequential treatment with a suitable silver salt, then a tertiary amine base in dimethylsulfoxide (DMSO) as shown in Scheme 2b.

Scheme 2a

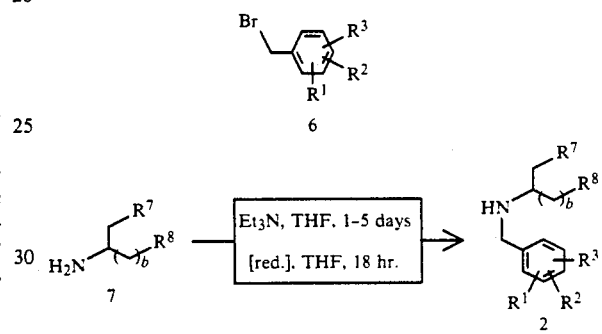

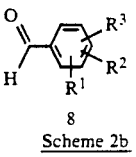

Scheme 2b

Amines, 5 or 7, are commercially available as α-amino esters where b=0, $R^8$=$CO_2R$, and $R^7$ is any of the substituents appropriate to the amino acid desired. A variety of additional $R^7$ substituents can be incorporated by numerous methods familiar to one skilled in the art. Some of these methods are summarized in Robert M. Williams, "Synthesis of Optically Active α-Amino Acids," Pergamon Press and references therein. For a treatise on manipulation of amino acids, see: "The Peptides", Volumes 1 and 3, E. Gross and J. Meienhofer, eds., Academic Press, Inc.

To prepare compounds of formula (I) where b=1 or 2 the amines, 5 or 7, can be homologated by a variety of methods familiar to one skilled in the art or these may be commercially available. For instance, a Wittig or Grignard reagent could be used to homologate the appropriately substituted aldehyde of 5.

If $R^7$ is a sulfur-containing group, this atom can be oxidized to the sulfoxide or sulfone by treatment with a variety of oxidative reagents to give 9. The preferred reagent is meta-chloroperoxybenzoic acid as shown in Scheme 3.

Scheme 3

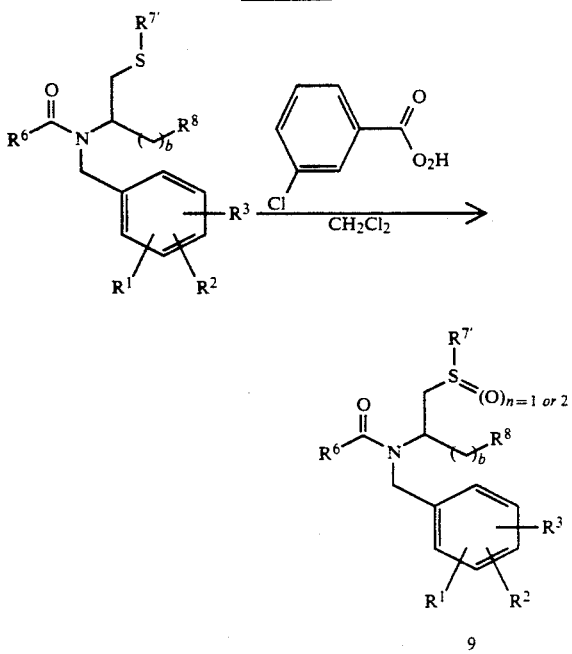

If $R^8$ is CHO or CH$_2$OH the acids or esters of the general formula (I) above can be treated with reducing agents known to those skilled in the art such as the borohydride or alkylaluminum hydride reducing agents. Alternatively, the amino alcohol of 5 may be commercially available in which case this can be oxidized to the aldehyde readily by treating with DMSO/sulfur trioxide pyridine complex.

The compounds of this invention and their preparation can be understood further by the following examples, which do not constitute a limitation of the invention.

EXAMPLE 1

Part A: Preparation of (S) N-[(2'-(triphenylmethyltetrazol-5-yl)biphenyl-4-yl) methyl]-phenylalanine t-butyl ester L-phenylalanine t-butyl ester hydrochloride (Bachem Bioscience, Inc.) (1.0 g, 3.9 mmol) was suspended in ethyl acetate, washed with saturated NaHCO$_3$ and brine, dried (MgSO$_4$), filtered and the solvent removed in vacuo. This residue was dissolved in 20 mL of THF and 1.95 g (3.5 mmol) of 2'-(N-triphenylmethyl tetrazol-5-yl)-4-bromomethylbiphenyl (prepared as described in EP 0 324 377) and 0.54 mL (3.9 mmol) triethylamine were added. The reaction was stirred at room temperature for 5 days. The THF was removed in vacuo and the residue dissolved in ethyl acetate. This was extracted 3× with K$_2$CO$_3$ and 1× with brine, dried over (MgSO$_4$), filtered, and the solvent removed in vacuo. The product was purified by silica gel chromatography eluting with ethyl acetate-hexanes to yield 0.61 g (25%) of a white glass.

| Mass (calc'd) | Mass (found) |
|---|---|
| 697 | 697 |

$^1$H NMR (300 MHz, CDCl$_3$ ) δ 6.8–7.9 (m, 28H); 3.6(ABq, 2H, J=14 Hz, Δν=52 Hz); 3.4(t, 1H), 2.9 (m, 2H); 1.4(s, 9H).

Part B: Preparation of (S) N-valeryl-N-[(2'-(triphenylmethyltetrazol-5-yl)biphenyl-4-yl)methyl]-phenylalanine t-butyl ester 0.425 g of the amine from Step A (0.61 mmol) was dissolved in 5 mL DMF. 0.15 mL valeryl chloride (1.22 mmol) and 0.32 mL diisopropylethylamine (2.44 mmol) were added, and the solution was stirred at room temperature overnight. The DMF was removed in vacuo and the residue was dissolved in ethyl acetate. This was extracted 3× with 0.1N HCl, 3× with saturated NaHCO$_3$ and 1× with brine. The organic layer was dried (MgSO$_4$), filtered and solvent removed in vacuo. The product was purified by silica gel chromatography elutin with ethyl acetate-hexanes to yield 0.13 g (27%) of a colorless oil.

| Mass (calc'd) | Mass (found) |
|---|---|
| 781 | 781 |

$^1$H NMR (300 MHz, CDCl$_3$ ) δ 6.9–7.9 (m, 28H); 3.9(ABq, 2H, J=16 Hz, Δν=210 Hz); 4.05(q, 1H, J=9 Hz, 6Hz); 3.25 (m, 2H); 2.2 (m, 2H); 1.6 (m, 2H); 1.4(s, 9H); 1.25 (m, 2H); 0.95 (m, 3H).

Part C: Preparation of (S) N-valeryl-N-[(2'-(1H-tetrazol-5-yl)biphenyl-4-yl)methyl]-phenylalanine 130 mg of the amide from Step B was treated with 5 mL 95% trifluoroacetic acid-H$_2$O for 1 h. The solvent was removed in vacuo and then 20 mL of ice water was added to the residue. 1N NaOH was added to pH ~11 and the solution was extracted 2× with ether. The aqueous layer was acidified to pH 2 with 3N HCl and extracted 3× with 1:1 ethyl acetate/n-butanol. The solvent was removed in vacuo to yield 90 mg (100% yield) of a colorless amorphous solid.

| Mass (calc'd) | Mass (found) |
|---|---|
| 483 | 483 |

$^1$H NMR (300 MHz, DMSO d$_6$) (Two conformers ~3:1) Major conformer: δ 6.9–7.6 (m, 13H); 4.4(t, 1H); 4.2(ABq, 2H, J=17 Hz, Δν=115 Hz); 3.15 (m, 2H); 2.1 (m, 2H); 1.4 (m, 2H); 1.14 (m, 2H); 0.8 (t, 3H). [α]$_D^{25}$= −41.9° (c=0.64, CHCl$_3$).

EXAMPLE 2

Part A: Preparation of [2'-(Triphenylmethyltetrazol-5-yl)biphenyl-4-yl]carboxaldehyde To a stirred, cooled (0° C.) solution of 18.6 g (33.4 mmol) of 2'-(N-triphenylmethyltetrazol-5-yl)-4-bromomethylbiphenyl in 160 mL of DMSO was added 17.0 g (61 mmol) of silver p-toluenesulfonate. The resulting slurry was warmed to ambient temperature with stirring over 1 h then re-cooled to 0° C. Triethylamine, 12 mL (86 mmol), was introduced, and the mixture was kept at −20° C. for 18 h. The reaction was warmed to ambient temperature and diluted with 300 mL of ether. This mixture was washed with 400 mL of 0.5N HCl, and the aqueous phase was back-extracted with 100 mL of $CH_2Cl_2$. The combined organic phases were washed with dilute aqueous $K_2CO_3$, then brine, and concentrated under reduced pressure to afford 15.8 g (95%) of an off-white solid.

$^1$H NMR (300 MHz, $CDCl_3$) δ 9.89(s, 1H); 6.87–8.08 (m, 23H).

Anal. Calc'd for $C_{33}H_{24}N_4O$: C, 80.47; H, 4.91; N, 11.37. Found: C, 80.24; H, 4.79; N, 11.65.

Part B: Preparation of (S) N-[(2'-(triphenylmethyltetrazol-5-yl)biphenyl-4-yl)methyl]-phenylalanine methyl ester To a stirred solution of 400 mg (0.81 mmol) of the aldehyde from Part A, 160 mg (0.74 mmol) of L-phenylalanine methyl ester, and 66 mg (0.81 mmol) of sodium acetate in 5 mL of DMF was added 0.50 mL of acetic acid followed by 6 mL of a 1M solution of $NaCNBH_3$ in THF. The solution was stirred at ambient temperature for 19 h, poured into aqueous $K_2CO_3$, and extracted with ethyl acetate then $CH_2Cl_2$. The combined organic extracts were washed with brine, dried ($MgSO_4$), concentrated under reduced pressure, and chromatographed on silica gel. Elution with 1:1 ethyl acetate-hexanes afforded, after removal of solvent, 380 mg (78%) of a colorless oil.

| Mass (calc'd) | Mass (found) |
|---|---|
| 655 | 655 |

$^1$H NMR (300 MHz, $CDCl_3$) δ 6.87–7.93 (m, 28H); 3.67(s, 3H); 3.62(ABq, 2H, $J_{AB}$=13.4 Hz, Δν=53 Hz); 3.55(t, 1H, J=6.2 Hz); 2.95(d, 2H, J=6.2 Hz). $[α]_D^{25}$ = −4.2° (c=0.47, $CHCl_3$).

Part C: Preparation of (S) N-butyryl-N-[(2'-(triphenylmethyltetrazol-5-yl)biphenyl-4-yl)methyl]-phenylalanine methyl ester To a stirred solution of 890 mg (1.36 mmol) of the amine from Part B and 0.42 mL (3 mmol) of triethylamine in 5 mL of THF was added 0.50 mL (3 mmol) of butyric anhydride. The reaction was stirred at ambient temperature for 26 h, after which time it was diluted with 20 mL of 1:1 ether-ethyl acetate. The solution was washed with 0.1N HCl, and the aqueous phase was back-extracted with $CH_2Cl_2$. The combined organic extracts were washed with dilute aqueous $K_2CO_3$, dried ($MgSO_4$), and concentrated under reduced pressure. The residual oil was evacuated at 0.05 torr for 3 days to achieve a constant mass of 800 mg (82%).

$^1$H NMR (300 MHz, $CDCl_3$) δ 6.88–7.9I(m, 28H); 4.18(dd, 1H, J=9.8, 5.8 Hz); 3.96(ABq, 2H, $J_{AB}$=16.5 Hz, Δν=187 Hz); 3.62(s, 3H); 3.27(ABx, 2H, $J_{AB}$=14.6 Hz, $J_{Ax}$=9.8 Hz, $J_{Bx}$=5.8 Hz); 2.14–2.24 (m, 2H); 1.53–1.71 (m, 2H); 0.87(t, 3H, J=7.3 Hz).

Part D: Preparation of (S) N-butyryl-N-[(2'-(1H-tetrazol-5-yl)biphenyl-4-yl)methyl]-phenylalanine To a stirred solution of 400 mg (0.55 mmol) of the methyl ester from Part C in 12 mL of THF was added 84 mg (2 mmol) of LiOH in 4 mL of water followed by 2 mL of methanol. The solution was stirred at ambient temperature for 1 h and then poured into water. The solution was acidified to pH 2 and extracted once with ethyl acetate and once with $CH_2Cl_2$. The combined organic extracts were dried ($MgSO_4$) and concentrated. The crude oil was dissolved in 20 mL of acetone and treated with 1 mL of 12N HCl. After stirring for 2 h at ambient temperature the solution was diluted with ethyl acetate and washed twice with dilute aqueous $K_2CO_3$. The combined aqueous washings were acidified to pH 2 and extracted with $CH_2Cl_2$ and then ethyl acetate. Drying ($MgSO_4$) and concentration under reduced pressure afforded 160 mg (62%) of a white foam.

| Mass (calc'd) | Mass (found) |
|---|---|
| 469 | 469 |

$^1$H NMR (300 MHz, $CDCl_3$) δ 6.99–7.95 (m, 14H); 4.00–4.06 (m, 1H); 3.94(ABq, 2H, $J_{AB}$=15.4 Hz, Δν=341 Hz); 3.28–3.48 (m, 2H); 2.37–2.42 (m, 2H); 1.63–1.72 (m, 2H); 0.96(t, 3H, J=7.3 Hz).

$[α]_D^{25}$ = −46.2° (c=0.61, $CHCl_3$).

Examples 3–32 shown in Table 1 may be prepared by the procedures described in Examples 1–2 from a suitable acid chloride or anhydride and the appropriately substituted amino ester.

TABLE 1

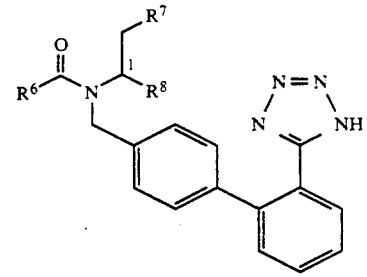

| Ex. No. | $R^6$ | $R^7$ | $R^8$ | Optical Center 1 | Physical Properties |
|---|---|---|---|---|---|
| 1 | n-butyl | $C_6H_5$ | $CO_2H$ | S | amorphous solid[a] |
| 2 | n-propyl | $C_6H_5$ | $CO_2H$ | S | white glass[b] |
| 3 | n-butyl | $C_6H_5$ | $CO_2H$ | R | white amorphous solid[c] |
| 4 | n-propyl | $C_6H_5$ | $CO_2H$ | R | white glass[d] |
| 5 | n-propyl | p-$C_6H_4OH$ | $CO_2H$ | S | |
| 6 | n-propyl | p-$C_6H_4OCH_3$ | $CO_2H$ | S | |
| 7 | n-butyl | p-$C_6H_4OH$ | $CO_2H$ | R | |
| 8 | n-butyl | p-$C_6H_4OCH_3$ | $CO_2H$ | R | |
| 9 | n-butyl | ethyl | $CO_2H$ | S | white amorphous solid[e] |
| 10 | n-butyl | ethyl | $CO_2H$ | R | white amorphous solid[f] |
| 11 | n-pentyl | ethyl | $CO_2H$ | S | white amorphous solid[g] |
| 12 | n-propyl | ethyl | $CO_2H$ | S | |
| 13 | n-propyl | ethyl | $CO_2H$ | R | |
| 14 | n-propyl | n-propyl | $CO_2H$ | S | |
| 15 | n-propyl | n-propyl | $CO_2H$ | R | |
| 16 | n-butyl | n-propyl | $CO_2H$ | S | |
| 17 | n-butyl | n-propyl | $CO_2H$ | R | |
| 18 | n-propyl | $CH_2SCH_3$ | $CO_2H$ | S | |
| 19 | n-propyl | $CH_2SCH_3$ | $CO_2H$ | R | |
| 20 | n-butyl | $CH_2SCH_3$ | $CO_2H$ | S | |
| 21 | n-butyl | $CH_2SCH_3$ | $CO_2H$ | R | |
| 22 | n-butyl | Sbenzyl | $CO_2H$ | R | white amorphous solid[h] |
| 23 | n-butyl | Sbenzyl | $CO_2H$ | S | |
| 24 | i-butyl | Sbenzyl | $CO_2H$ | R | white amorphous solid[i] |

TABLE 1-continued

[Structure: R⁶-C(=O)-N(CH₂-aryl)-CH(R⁸)(CH₂R⁷) with biphenyl-tetrazole group]

| Ex. No. | R⁶ | R⁷ | R⁸ | Optical Center 1 | Physical Properties |
|---------|-----|-----|-----|------------------|--------------------|
| 25 | n-propyl | SCH₂-p-C₆H₄CH₃ | CO₂H | R | |
| 26 | n-propyl | SCH₂-p-C₆H₄CH₃ | CO₂H | S | |
| 27 | n-butyl | SCH₂-p-C₆H₄CH₃ | CO₂H | R | |
| 28 | n-butyl | SCH₂-p-C₆H₄CH₃ | CO₂H | S | |
| 29 | n-propyl | SCH₂-p-C₆H₄OCH₃ | CO₂H | R | |
| 30 | n-propyl | SCH₂-p-C₆H₄OCH₃ | CO₂H | S | |
| 31 | n-butyl | SCH₂-p-C₆H₄OCH₃ | CO₂H | R | |
| 32 | n-butyl | SCH₂-p-C₆H₄OCH₃ | CO₂H | S | |

<sup>a</sup>Mass (calc'd) Mass (found)
483    483
¹H NMR(300MHz, DMSO d₆) (Two conformers ~3:1) Major conformer: δ6.9–7.6(m, 13H); 4.4(t, 1H); 4.2(ABq, 2H, J=17Hz, Δν=115Hz); 3.15(m, 2H); 2.1(m, 2H); 1.4(m, 2H); 1.15(m, 2H); 0.8(t, 3H). $[\alpha]_D^{25}$ = –41.9°(c=0.64, CHCl₃).
<sup>b</sup>Mass (calc'd) Mass (found)
469    469
¹H NMR(300MHz, CDCl₃) δ6.99–7.95(m, 14H); 4.00–4.06(m, 1H); 3.94(ABq, 2H, J_{AB}=15.4Hz, Δν=341Hz); 3.28–3.48(m, 2H); 2.37–2.42(m, 2H); 1.63–1.72(m, 2H); 0.96(t, 3H, J=7.3Hz). $[\alpha]_D^{25}$ = –46.2°(c=0.61, CHCl₃).
<sup>c</sup>Mass (calc'd) Mass (found)
483    483
¹H NMR(300MHz, DMSO d₆) (Two conformers ~3:1) Major conformer: δ6.9–7.6(m, 13H); 4.4(t, 1H); 4.2(ABq, 2H, J=17Hz, Δν=115Hz); 3.15(m, 2H); 2.1(m, 2H); 1.4(m, 2H); 1.15(m, 2H); 0.8(t, 3H). $[\alpha]_D^{25}$ = +37.1°(c=0.57, CHCl₃).
<sup>d</sup>¹H NMR(300MHz, CDCl₃) δ6.99–7.95(m, 14H); 4.00–4.06(m, 1H); 3.94(ABq, 2H, J=15.4Hz, Δν=341Hz); 3.28–3.48(m, 2H); 2.37–2.42(m, 2H); 1.63–1.72(m, 2H); 0.96(t, 3H, J=7.3Hz).
<sup>e</sup>Mass (calc'd) Mass (found)
435    435
¹H NMR(300MHz, CDCl₃) (two conformers ~4:1) Major conformer: δ7.00–8.02(m, 8H); 4.58(ABq, 2H, J_{AB}=15.4Hz, Δν=79Hz); 4.21(t, 1H, J=7.5Hz); 2.53(t, 2H, J=7.5Hz); 1.81–2.09(m, 2H); 1.62–1.75(m, 2H); 1.29–1.43(m, 4H); 0.89–0.99(m, 6H). $[\alpha]_D^{25}$ = +7.5°(c=0.28, CHCl₃).
<sup>f</sup>¹H NMR(300MHz, CDCl₃) (two conformers ~4:1) Major conformer: δ7.00–8.02(m, 9H); 4.58(ABq, 2H, J_{AB}=15.4Hz, Δν=79Hz); 4.21(t, 1H, J=7.5Hz); 2.53(t, 2H, J=7.5Hz); 1.81–2.09(m, 2H); 1.62–1.75(m, 2H); 1.29–1.43(m, 4H); 0.89–0.99(m, 6H).
<sup>g</sup>¹H NMR(300MHz, CDCl₃) δ7.03–8.07(m, 8H); 4.60(ABq, 2H, J_{AB}=15.7Hz, Δν=75Hz); 4.19(t, 1H, J=7.5Hz); 2.56(t, 2H, J=7.5Hz); 1.24–2.06(m, 10H); 0.84–0.98(m, 6H).
<sup>h</sup>¹H NMR(300MHz, DMSO d₆) (two conformers ~5:1) Major conformer: δ6.94–7.72(m, 13H); 4.62(ABq, 2H, J_{AB}=18.0Hz, Δν=49Hz); 4.38(dd, 1H, J=7.6, 5.8Hz); 3.66(d, 2H, J=2.2Hz); 2.88(ABx, 2H, J_{AB}=14.2Hz, J_{Ax}=7.6Hz, J_{Bx}=5.8Hz, Δν=60Hz); 2.04–2.34(m, 2H); 1.10–1.44(m, 4H); 0.78(t, 3H, J=7.2Hz).
<sup>i</sup>Mass (calc'd) Mass (found)
529    529
¹H NMR(300MHz, DMSO d₆) (two conformers ~5:1) Major conformer: δ6.95–7.70(m, 14H); 4.63(ABq, 2H, J_{AB}=17.6Hz, Δν=52Hz); 4.3(dd, 1H, J=7.5, 5.8Hz); 3.65(d, 2H, J=1.8Hz); 2.88(ABx, 2H, J_{AB}=14.0Hz, J_{Ax}=7.5Hz, J_{Bx}=5.8Hz, Δν=66Hz); 1.87–2.22(m, 3H); 0.79–0.91(m, 6H). $[\alpha]_D^{25}$ = –28.2°(c=0.26, CHCl₃).

The following examples show the preparation of other compounds of the invention which are then further illustrated in Table 2.

EXAMPLE 33

Part A: Preparation of (S) N-[(2'-(triphenylmethyltetrazol-5-yl)biphenyl-4-yl)methyl]-norvaline ethyl ester To a stirred solution of 900 mg (6.20 mmol) of norvaline ethyl ester, 2.22 g (4.5 mmol) of the aldehyde from Example 2, Part A and 0.40 mL of acetic acid in 20 mL of DMF was added 20 mL (20 mmol) of a 1.0M solution of sodium cyanoborohydride in THF. The solution was stirred at ambient temperature for 16 h and then diluted with 100 mL of 2:1 ether-ethyl acetate. This solution was washed with 100 mL of 0.3N HCl, and the aqueous phase was extracted with CH₂Cl₂. The combined organic phases were washed with dilute aqueous K₂CO₃, then brine, and dried (MgSO₄). Concentration under reduced pressure afforded an oil which was chromatographed on silica gel. Elution with 1:1 ethyl acetate-hexanes afforded 1.90 g (69%) of a viscous oil.

¹H NMR (300 MHz, CDCl₃) δ 6.85–7.93(m, 23H); 4.20(q, 2H, J=7.3 Hz); 3.62(ABq, 2H, J_{AB}=12.8 Hz, Δν=56.4 Hz); 3.25(t, 1H, J=6.8 Hz); 1.55–1.64(m, 2H); 1.33–1.44(m, 2H); 1.29(t, 3H, J=7.3 Hz); 0.90(t, 2H, J=7.3 Hz).

Anal. Calc'd for C₄₀H₃₉N₅O₂: C, 77.27; H, 6.32; N, 11.26. Found: C, 76.89; H, 6.18; N, 11.11. $[\alpha]_D^{25}$ = –12.50° (c=1.00, CHCl₃).

Part B: Preparation of (S) N-valeryl-N-[(2'-(triphenylmethyltetrazol-5-yl)biphenyl-4-yl)methyl]-norvaline ethyl ester To a stirred solution of 200 mg (0.327 mmol) of the amine from Part A and 0.70 mL (0.5 mmol) of triethylamine in 5 mL of CH₂Cl₂ was added 0.60 mL (0.5 mmol) of valeryl chloride. The solution was stirred at ambient temperature for 18 h and diluted with ether. This solution was washed with 0.1M HCl, dilute aqueous K₂CO₃, then brine and dried. Concentration afforded a glass which was chromatographed on silica gel. The product was eluted with 1:1 ethyl acetate-hexanes to afford, after removal of solvent, 195 mg (86%) of a colorless oil.

¹H NMR (300 MHz, DMSO d₆) (two conformers, ~4:1)
Major conformer: δ 6.85–7.79(m, 23H); 4.54(ABq, 2H, J_{AB}=17.5 Hz, Δν=58 Hz); 4.28(dd, 1H, J=6.7, 6.2 Hz); 3.91–3.97(m, 2H); 2.08–2.47(m, 2H); 1.06–1.87(m, 11H); 0.72–0.93(m, 6H).

Part C: Preparation of (S) N-valeryl-N-[(2'-(1H-tetrazol-5-yl)biphenyl-4-yl)methyl]-norvaline ethyl ester To a stirred solution of 180 mg (0.255 mmol) of the trityl tetrazole from Part B in 10 mL of acetone was added 0.5 mL of 12N HCl. The solution was stirred at ambient temperature for 1 h and diluted with 20 mL of ether. The mixture was brought to pH 10 by addition of dilute aqueous K₂CO₃, and the phases were separated. The organic phase was washed twice with diluted with K₂CO₃ solution, and the combined aqueous washings were acidified to pH 2 with 12N HCl. The colloidal suspension was extracted three times with CHCl₃, and the combined organic extracts were dried (MgSO₄), concentrated, and lyophilized from benzene to afford 118 mg (79%) of a powder.

¹H NMR (300 MHz, CDCl₃) (two conformers, ~1:1) δ 7.09–8.16(m, 9H); 4.4–4.77(m, 3H); 3.91–4.13(m, 2H); 2.18–2.35(m, 2H); 1.57–2.04(m, 4H); 1.18–1.42(m, 7H); 1.83–1.88(m, 6H).

EXAMPLE 34

Part A: Preparation of (S) N-[(2'-(triphenylmethyltetrazol-5-yl)biphenyl-4-yl)methyl]-leucine ethyl ester To a stirred solution of 2.35 g (12 mmol) of leucine ethyl ester hydrochloride, 4.93 g (10 mmol) of the aldehyde from Example 2, Part A and 0.80 mL of acetic acid in 40 mL of DMF was added 50 mL (50 mmol) of a 1.0M solution of sodium cyanoborohydride in THF. The solution was stirred at ambient temperature for 16 h and then diluted with 100 mL of 2:1 ether-ethyl acetate. This solution was washed with 100 mL of 0.3N HCl, and the aqueous phase was extracted with $CH_2Cl_2$. The combined organic phases were washed with dilute aqueous $K_2CO_3$, then brine, and dried ($MgSO_4$). Concentration under reduced pressure afforded an oil which was chromatographed on silica gel. Elution with 1:1 ethyl acetate-hexanes afforded 4.52 g (72%) of a viscous oil.

$^1$ H NMR (300 MHz, $CDCl_3$) δ 6.85-7.93(m, 23H); 4.20(q, 2H, J=7.3 Hz); 3.62(ABq, 2H, $J_{AB}$=12.8 Hz, Δν=56.4 Hz); 3.25(t, 1H, J=6.8 Hz); 1.55-1.64(m, 2H); 1.33-1.44(m, 2H); 1.29(t, 3H, J=7.3 Hz); 0.90(t, 2H, J=7.3 Hz).

Part B: Preparation of (S) N-butyryl-N-[(2'-(1H-tetrazol-5-yl)biphenyl-4-yl)methyl]-leucine ethyl ester To a stirred solution of 316 mg (0.50 mmol) of the amine from Part A and 0.33 mL (3.0 mmol) of N-methylmorpholine in 10 mL of $CH_2Cl_2$ was added 0.41 mL (2.5 mmol) of butyric anhydride. The solution was stirred at ambient temperature for 18 h and diluted with ether. This solution was washed with 0.1M HCl, dilute aqueous $K_2CO_3$, then brine, dried ($MgSO_4$), and concentrated. The crude product was dissolved in 10 mL of acetone and treated with 0.3 mL of 12N HCl. The solution was stirred at ambient temperature for 1 h and diluted with 20 mL of ether. The mixture was brought to pH 10 by addition of dilute aqueous $K_2CO_3$, and the phases were separated. The organic phase was washed three times with dilute $K_2CO_3$ solution, and the combined aqueous washings were acidified to pH 2 with 12N HCl. The colloidal suspension was extracted twice with $CHCl_3$, and the combined organic extracts were dried ($MgSO_4$), concentrated, and lyophilized from benzene to afford 180 mg (91%) of a powder.

$^H$NMR (300 MHz, $CDCl_3$) (two conformers, ~1:1) δ 7.13-8.22(m, 8H); 4.46-4.88(m, 3H); 3.91-4.14(m, 2H); 2.24-2.54(m, 2H); 1.47-1.93(m, 5H); 1.20(t, 3H, J=7.3 Hz); 0.81-0.99(m, 9H).

EXAMPLE 35

Preparation of (R) N-(isobutoxycarbonyl)-N-[(2'-(1H-tetrazol-5-yl)biphenyl-4-yl)methyl]-S-benzylcysteine To a stirred, cooled (−23° C.) solution of 303 mg (2.00 mmol) of 1-(carboxymethyl)-2,5-dimethylpyrrole and 0.22 mL (2.0 mmol) of N-methylmorpholine in 5 mL of THF was added 0.25 mL (1.95 mmol) of isobutyl chloroformate. The solution was stirred at −23° C. for 5 min. and a solution of 600 mg (0.855 mmol) of the intermediate secondary amine from Example 22 in 5 mL of THF was introduced. This solution was stirred at room temperature for 1 h, stirred at reflux for 2 h, then cooled to ambient temperature. The reaction was diluted with 20 mL of ether and washed with 0.1N HCl. The aqueous washing was back-extracted with $CHCl_3$, and the combined organic extracts were washed three times with dilute aqueous $K_2CO_2$. The solution was dried ($MgSO_4$), concentrated under reduced pressure, and chromatographed on silica gel. Elution with 1:1 ethyl acetate-hexanes afforded, in addition to the expected amide, a carbamate by-product of higher $R_f$ which was deprotected as follows. The carbamate was dissolved in 10 mL of acetone and stirred with 0.6 mL of 12N HCl for 1 h. The reaction was diluted with ether and washed three times with dilute aqueous $K_2CO_3$. The combined aqueous washings were acidified to pH 2 and extracted twice with $CHCl_3$. The combined organic extracts were dried ($MgSO_4$), concentrated under reduced under pressure, and redissolved in 10 mL of THF. This solution was treated with 5 mL of 0.2M aqueous LiOH and the mixture was stirred 1 h. The reaction was diluted with ether and washed three times with dilute aqueous $K_2CO_2$. The combined aqueous washings were acidified to pH 2, and extracted once with $CHCl_3$, and once with 1:1 ethyl acetate-ether. The combined organic extracts were dried ($MgSO_4$), concentrated, and lyophilized from benzene to afford 22 mg (5%) of a white powder.

| Mass (calc'd) | Mass (found) |
|---|---|
| 545 | 545 |

$^H$ NMR (300 MHz, DMSO $d_6$) δ 7.01-7.70(m, 14H); 4.23-4.70(m, 3H); 3.60-3.83(m, 4H); 2.72-3.03(m, 2H); 1.64-1.83(m, 1H); 0.84(d, 3H, J=6.7 Hz); 0.71(d, 3H, J=6.5 Hz).

TABLE 2

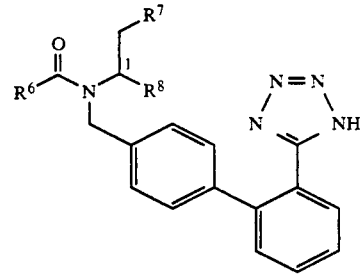

| Ex. No. | $R^6$ | $R^7$ | $R^8$ | Optical Center 1 | Physical Properties |
|---|---|---|---|---|---|
| 33 | n-butyl | ethyl | $CO_2Et$ | S | amorphous solid$^a$ |
| 34 | n-propyl | i-butyl | $CO_2Et$ | S | amorphous solid$^b$ |
| 35 | i-butyloxy | Sbenzyl | $CO_2H$ | R | white amorphous solid$^c$ |

$^a$$^1$H NMR(300MHz, $CDCl_3$) (two conformers ~1:1) δ7.09-8.16(m, 9H); 4.4-4.77(m, 3H); 3.91-4.13(m, 2H); 2.18-2.35(m, 2H); 1.57-2.04(m, 4H); 1.18-1.42(m, 7H); 1.83-1.88(m, 6H).
$^b$$^1$H NMR(300MHz, $CDCl_3$) (two conformers ~1:1) δ7.13-8.22(m, 8H); 4.46-4.88(m, 3H); 3.91-4.14(m, 2H); 2.24-2.54(m, 2H); 1.47-1.93(m, 5H); 1.20(t, 3H, J=7.3Hz); 0.81-0.99(m, 9H).
$^c$Mass (calc'd) Mass (found)
545 545
$^1$H NMR(300MHz, DMSO $d_6$) δ7.01-7.70(m, 14H); 4.23-4.70(m, 3H); 3.60-3.83(m, 4H); 2.72-3.03(m, 2H); 1.64-1.83(m, 1H); 0.84(d, 3H, J=6.7Hz); 0.71(d, 3H, J=6.5Hz).

EXAMPLE 36

Preparation of (R) N-valeryl-N-[(2'-(1H-tetrazol-5-yl)biphenyl-4-yl)methyl]-S,S-dioxy-S-benzylcysteine To a stirred solution of 30 mg (0.057 mmol) of the thiol from Example 35 in 5 mL of $CH_2Cl_2$ was added 60 mg (0.35 mmol) of meta-chloroperoxybenzoic acid. The solution was stirred at ambient temperature for 2 h and concentrated. The crude solid product was chromatographed on silica gel (elution with 85:10:5 $CHCl_3$/methanol/acetic acid) to afford 16 mg (50%) of the desired sulfone as a white foam.

[1] H NMR (300 MHz, DMSO $d_6$) Multiple conformers: δ 6.96–7.58(m, 14H); 4.39–4.84(m, 5H); 4.40–4.95(m, 2H); 2.08–2.49(m, 2H); 1.11–1.57(m, 4H); 0.77–0.93(m, 3H).

With the proper selection of reactants, one skilled in the art utilizing the procedure described in Example 36 above, may prepare the compounds of Examples 37–49 shown in Table 3 below:

TABLE 3

| Ex. No. | $R^6$ | $R^7$ | $R^8$ | Optical Center 1 | Physical Properties |
|---|---|---|---|---|---|
| 36 | n-propyl | S(O)$_2$benzyl | CO$_2$H | R | white glass[a] |
| 37 | n-butyl | S(O)$_2$benzyl | CO$_2$H | S | |
| 38 | n-propyl | CH$_2$S(O)$_2$CH$_3$ | CO$_2$H | S | |
| 39 | n-propyl | CH$_2$S(O)$_2$CH$_3$ | CO$_2$H | R | |
| 40 | n-butyl | CH$_2$S(O)$_2$CH$_3$ | CO$_2$H | S | |
| 41 | n-butyl | CH$_2$S(O)$_2$CH$_3$ | CO$_2$H | R | |
| 42 | n-propyl | S(O)$_2$CH$_2$-p-C$_6$H$_4$CH$_3$ | CO$_2$H | R | |
| 43 | n-propyl | S(O)$_2$CH$_2$-p-C$_6$H$_4$CH$_3$ | CO$_2$H | S | |
| 44 | n-butyl | S(O)$_2$CH$_2$-p-C$_6$H$_4$CH$_3$ | CO$_2$H | R | |
| 45 | n-butyl | S(O)$_2$CH$_2$-p-C$_6$H$_4$CH$_3$ | CO$_2$H | S | |
| 46 | n-propyl | S(O)$_2$CH$_2$-p-C$_6$H$_4$OCH$_3$ | CO$_2$H | R | |
| 47 | n-propyl | S(O)$_2$CH$_2$-p-C$_6$H$_4$OCH$_3$ | CO$_2$H | S | |
| 48 | n-butyl | S(O)$_2$CH$_2$-p-C$_6$H$_4$OCH$_3$ | CO$_2$H | R | |
| 49 | n-butyl | S(O)$_2$CH$_2$-p-C$_6$H$_4$OCH$_3$ | CO$_2$H | S | |

[a] $^1$H NMR(300 MHz, DMSO $d_6$) Multiple conformers: δ6.96–7.58(m, 14H); 4.39–4.84(m, 5H); 4.40–4.95(m, 2H); 2.08–2.49(m, 2H); 1.11–1.57(m, 4H); 0.77–0.93(m, 3H).

Utility

AII produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Chiu, et. al., Receptor, 1 33, (1990)]. In brief, aliquots of a freshly prepared particulate fraction of rat adrenal cortex were incubated with 0.05 nM [$^{125}$I] AII and varying concentrations of potential AII antagonists in a Tris buffer. After a 1 h incubation the reaction was terminated by addition of cold assay buffer. The bound and free radioactivity were rapidly separated through glass-fiber filters, and the trapped radioactivity was quantitated by scintillation counting. The inhibitory concentration (IC$_{50}$) of potential AII antagonists which gives 50% displacement of the total specifically bound [$^{125}$I]AII is presented as a measure of the affinity of such compound for the AII receptor.

Using the assay method described above, the compounds of this invention are found to exhibit an activity of at least IC$_{50}$<10 micromolar, thereby demonstrating an confirming the activity of these compounds as effective AII antagonists.

The potential antihypertensive effects of the compounds of this invention may be demonstrated by administering the compounds to awake rats made hypertensive by ligation of the left renal artery [Cangiano, et al., J. Pharmacol. Exp. Ther, 208, 310 (1979)]. This procedure increases blood pressure by increasing renin production with consequent elevation of AII levels. Compounds are administered intravenously via a cannula in the jugular vein to give a cumulative dose of 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds.

Using the in vivo methodology described above, the compounds of this invention are found to exhibit an activity (intravenous) which is 10 mg/kg or less, and/or an activity (oral) which is 100 mg/kg or less, thereby demonstrating and confirming the utility of these compounds as effective agents in lowering blood pressure.

The compounds of the invention are useful in treating hypertension. They are also of value in the management of acute and chronic congestive heart failure and angina. These compounds may also be expected to be useful in the treatment of primary and secondary hyperaldosteronism; renal diseases such as diabetic nephropathy, glomerulonephritis, glomerular sclerosis, nephrotic syndrome, hypertensive nephrosclerosis, end stage renal disease, used in renal transplant therapy, and to treat renovascular hypertension, scleroderma, left ventricular dysfunction, systolic and diastolic dysfunction, diabetic retinopathy and in the management of vascular disorders such as migraine, Raynaud's disease, and as prophylaxis to minimize the atherosclerotic process and neointimal hyperplasia following angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, β-adrenergic antagonists such as timolol maleate, adrenergic agonists such as epinephrine and carbonic anhydrase inhibitors such as MK-507.

In the management of hypertension and the clinical conditions noted above, the compounds of this invention may be utilized with a pharmaceutical carrier in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets being followed by a patient, concurrent medication, and other factors which those skilled in the art will recognize, the dosage range will generally be about 1 to 1000 mg per patient per day which can be administered in single or multiple doses. Preferably, the dosage range will be about 5 to 500 mg per patient per day; more preferably about 5 to 300 mg per patient per day.

The compounds of this invention can also be administered in combination with other antihypertensives and/or diuretics. For example, the compounds of this invention can be given in combination with diuretics such as hydrochlorothiazide, chlorothiazide, chlorthalidone, methylclothiazide, furosemide, ethacrynic acid, triamterene, amiloride spironolactone and atriopeptin; calcium channel blockers, such as diltiazem, felodipine, nifedipine, amlodipine, nimodipine, isradipine, nitrendipine and verapamil; $\beta$-adrenergic antagonists such as timolol, atenolol, metoprolol, propanolol, nadolol and pindolol; ACE inhibitors such as enalapril, lisinopril, captopril, ramipril, quinapril and zofenopril; renin inhibitors such as A-69729, FK 906 and FK 744; $\alpha$-adrenergic antagonists such as prazosin, doxazosin, and terazosin; sympatholytic agents such as methyldopa, clonidine and guanabenz; atriopeptidase inhibitors (alone or with ANP) such as UK-79300; serotonin antagonists such as ketanserin; $A_2$-adrenosine receptor agonists such as CGS 22492C; potassium channel agonists such as pinacidil and cromakalim; and various other antihypertensive drugs including reserpine, minoxidil, guanethidine, hydralazinc hydrochloride and sodium nitroprusside as well as combinations of the above-named drugs. Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly. To illustrate these combinations, one of the angiotensin II antagonists of this invention effective clinically in the 5–500 milligrams per day range can be effectively combined at levels at the 1.0–500 milligrams per day range with the following compounds at the indicated per day dose range: hydrochlorothiazide (6–100 mg), chlorothiazide (125–500 mg), ethacrynic acid (5–200 mg), amiloride (5–20 mg), furosemide (5–80 mg), propranolol (10–480 mg), timolol maleate (1–20 mg), methyldopa (125–2000 mg), felodipine (1–20 mg), nifedipine (5–120 mg), nitrendipine (5–60 mg), and diltiazem (30–540 mg). In addition, triple drug combinations of hydrochlorothiazide (5–100 mg) plus amiloride (5–20 mg) plus angiotensin II antagonists of this invention (1–500 mg) or hydrochlorothiazide (5–100 mg) plus timolol maleate (5–60 mg) plus an angiotensin II antagonists of this invention (1–500 mg) or hydrochlorothiazide (5–200 mg) and nifedipine (5–60 mg) plus an angiotensin II antagonist of this invention (1–500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The compounds of this invention also may exhibit central nervous system (CNS) activity. They may be useful in the treatment of cognitive dysfunctions including Alzheimer's disease, amnesia and senile dementia. These compounds may also have anxiolytic and antidepressant properties and could therefore, be useful in the relief of symptoms of anxiety and tension and in the treatment of patients with depressed or dysphoric mental states.

Further, these compounds may exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

As indicated above, the active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

What is claimed is:

1. A compound of formula (I)

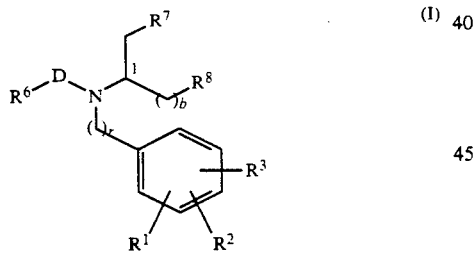

(I)

wherein:

$R^1$ is other than in the ortho position and is

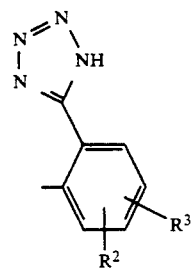

$R^2$ and $R^3$ are independently:
  (a) H,
  (b) halo,
  (c) $C_1$-$C_4$ alkyl,
  (d) $C_1$-$C_4$ alkoxy,
  (e) $C_1$-$C_4$ alkoxyalkyl;

$R^5$ is
  (a) H,
  (b) $C_1$-$C_6$ alkyl,
  (c) $C_3$-$C_6$ cycloalkyl,
  (d) $C_2$-$C_4$ alkenyl,
  (e) $C_2$-$C_4$ alkynyl;

$R^6$ is
  (a) $C_1$-$C_{10}$ alkyl,
  (b) $C_3$-$C_{10}$ alkenyl,
  (c) $C_3$-$C_{10}$ alkynyl,
  (d) $C_3$-$C_8$ cycloalkyl,
  (e) $C_4$-$C_8$ cycloalkenyl,
  (f) $C_4$-$C_{10}$ cycloalkylalkyl,
  (g) $C_5$-$C_{10}$ cycloalkylalkenyl,
  (h) $C_5$-$C_{10}$ cycloalkylalkynyl,
  (i) $-(CH_2)_2Z^2(CH_2)_mR^5$,
  (j) benzyl, optionally substituted on the phenyl ring with 1-2 substituents selected from the group of halo, $C_1$-$C_4$ alkyl, $C_1$-$C_4$ alkoxy, $-$OH or $-NO_2$, $R^7$ is
  (a) $C_1$-$C_6$ alkyl,
  (b) $C_3$-$C_6$ cycloalkyl,
  (c) $C_2$-$C_{10}$ perfluoroalkyl,
  (d) $COR^+$,
  (e) aryl,
  (f) $C_1$-$C_3$ alkylaryl,
  (g) $-(CH_2)_nS(O)_gCH_2$phenyl, where phenyl is optionally substituted with 1-2 substituents selected from the group of halo, $-$OH, $C_1$-$C_3$ alkoxy, or $C_1$-$C_3$ alkyl,
  (h) $-CH_2S(O)_gCH_3$, wherein aryl is as defined above and 1- or 2-naphthyl;

$R^8$ is
  (a) $-CO_2H$,
  (b) $-CO_2R^{40}$,
  (c) $-CHO$,
  (d) $-CH_2OH$,
  (e) $-CH_2OC(O)(CH_2)_nCO_2H$,
  (f) $-CN$,
  (g) $-SO_3H$,
  (h) $-SO_2OR^{40}$,
  (i) -tetrazol-5-yl,
  (j) $-PO_3H_2$,
  (k) $-P(O_2)OR^{40}$;

$R^{30}$ is
  (a) H,
  (b) $C_1$-$C_5$ alkyl,
  (c) $OR^{12}$;

$R^{40}$ is
  (a) $C_1$-$C_6$ alkyl,
  (b) $C_1$-$C_6$ perfluoroalkyl,
  (c) 1-adamantyl,
  (d) 1-naphthyl,
  (e) benzyl;

D is
  (a) $-CO-$,
  (b) $-CS-$,
  (c) $-SO_2-$;

$Z^2$ is
  (a) $-O-$,
  (b) $-S-$,
  (c) $-NR^{11}-$;

g is 0 to 2,
m is 1 to 5,
n is 0 to 1, s is 0 to 5, r is 1 to 2, b is 0 to 2, or a pharmaceutically acceptable salt thereof.

2. A compound of claim 1 wherein:

$R_2$ is
- (a) H,
- (b) halo,
- (c) $C_1$-$C_{alkyl}$,
- (d) $C_1$-$C_4$ alkoxy;

$R^6$ is
- (a) $C_2$-$C_7$ alkyl,
- (b) $C_2$-$C_7$ alkoxy;

$R^8$ is
- (a) —$CO_2H$,
- (b) —$CO_2CH_3$,
- (c) —$CO_2CH_2CH_3$,
- (d) —CHO,
- (e) —$CH_2OH$;

D is —CO—;

b=0;

or a pharmaceutically acceptable salt thereof.

3. A compound of claim 2 selected from the group consisting of:

(S) N-valeryl-N-[(2'-(1H-tetrazol-5-yl)biphenyl-4-yl)methyl]-phenylalanine (R) N-butyryl-N-[(2'-(1H-tetrazol-5-yl)biphenyl-4-yl)methyl]-phenylalanine (S) N-butyryl-N-[(2,-(1H-tetrazol-5-yl)biphenyl-4-yl)methyl]-phenylalanine (R) N-isovaleryl-N-[(2'-(1H-tetrazol-5-yl)biphenyl-4-yl)methyl]-S-benzylcysteine (R) N-valeryl-N-[(2'-(1H-tetrazol-5-yl)biphenyl-4-yl)methyl]-S,S-dioxy-S-benzylcysteine (R) N-valeryl-N-[(2'-(1H-tetrazol-5-yl)biphenyl-4-yl)methyl]-norvaline.

4. A pharmaceutical composition comprising a pharmaceutically suitable carrier and a compound of claim 3.

5. A method of treating hypertension in a warm blooded animal comprising administering to an animal in need of such treatment an effective amount of a compound of claim 3.

6. A method of treating congestive heart failure in a warm blooded animal comprising administering to an animal in need of such treatment an effective amount of a compound of claim 3.

* * * * *